(12) United States Patent
Su et al.

(10) Patent No.: US 7,005,264 B2
(45) Date of Patent: Feb. 28, 2006

(54) METHOD AND APPARATUS FOR NUCLEIC ACID SEQUENCING AND IDENTIFICATION

(75) Inventors: Xing Su, Cupertino, CA (US); Andrew A. Berlin, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 347 days.

(21) Appl. No.: 10/153,125

(22) Filed: May 20, 2002

(65) Prior Publication Data

US 2006/0019247 A1 Jan. 26, 2006

(51) Int. Cl.
*C12Q 1/68* (2006.01)
*C12P 19/34* (2006.01)

(52) U.S. Cl. .............................. 435/6; 435/6; 435/91.1; 435/91.2

(58) Field of Classification Search ..................... 435/6, 435/91.1, 91.2
See application file for complete search history.

(56) References Cited

U.S. PATENT DOCUMENTS

| | | |
|---|---|---|
| 4,962,037 A | 10/1990 | Jett et al. |
| 5,306,403 A | 4/1994 | Vo-Dinh |
| 5,332,666 A | 7/1994 | Prober et al. |
| 5,405,747 A | 4/1995 | Jett et al. |
| 5,436,130 A | 7/1995 | Mathies et al. |
| 5,721,102 A | 2/1998 | Vo-Dinh |
| 5,776,674 A | 7/1998 | Ulmer |
| 5,783,389 A | 7/1998 | Vo-Dinh |
| 5,814,516 A | 9/1998 | Vo-Dinh |
| 5,821,058 A | 10/1998 | Smith et al. |
| 5,866,336 A | 2/1999 | Nazarenko et al. |
| 6,002,471 A | 12/1999 | Quake |
| 6,146,227 A | 11/2000 | Mancevski |
| 6,174,677 B1 | 1/2001 | Vo-Dinh |
| 6,210,896 B1 | 4/2001 | Chan |
| 6,514,767 B1 | 2/2003 | Natan |
| 6,627,067 B1 * | 9/2003 | Branton et al. ............. 205/778 |
| 6,673,615 B1 * | 1/2004 | Denison et al. ................ 436/2 |

OTHER PUBLICATIONS

"Nanopore Technology, Probing Polynucleotides with a Nanopore: High Speed, Single Molecule DNA Sequencing," Branton Lab—Nanopore Sequencing Description, 3 pages, downloaded from the internet on Feb. 3, 2002.
Kasianowicz et al., "Characterization of Individual Polynucleotide Molecules Using a Membrane Channel," *Pro. Natl. Acad. Sci. USA*, vol. 93. pp. 13770-13773, Nov. 1996.
Ashby, et al., "Probing Intermolecular Forces and Potentials with Magnetic Feedback", *J. Am. Chem. Soc.* 122:9467-9472, (2000).
Cui, et al., "Doping and Electrical Transport in Silicon Nanowires", *J. of Phys. Chem.* B 104(22):5213-5216, (2000).
Cheung, et al., "Carbon Nanotube Atomic Force Microscopy Tips: Direct Growth by Chemical Vapor Deposition and Application to High-Resolution Imaging", *PNAS*, 97(8): 3809-3813, (2000).
Cheung, et al., "Growth and Fabrication with Single-Walled Carbon Nanotube Probe Microscopy Tips", *Appl. Phys. Lett.* 76(21):3136-3138.
Doering, et al., "Spectroscopic Tags Using Dye-Embedded Nanoparticles and Surface—Enhanced Raman Scattering", *Analytical Chemistry*, :5-9.
Duan, et al., "Synthesis and Optical Properties of Gallium Arsenide Nanowires", *Appl. Phys. Lett.* 76(9):1116-1118, (Feb. 2000).
Duan, et al., "General Synthesis of Compound Semiconductor Nanowires", *Adv. Mater.* 12(4):298-302, (2000).
Duan, et al., "Laser-Assisted Catalytic Growth of Single Crystal GaN Nanowires", *J. Am. Chem. Soc.* 122:188-189, (2000).
Gudiksen, et al., "Diameter-Selective Synthesis of Semiconductor Nanowires," *J. Am. Chem. Soc.* 122:8801-8802, (2000).
Hu, et al., "Nitrogen-Driven $sp^3$ to $sp^2$ Transformation in Carbon Nitride Materials", *Am. Chem. Phys. Soc.* 57(6): R3185-R3188, (1998).
Hu, et al., "Nitrogen-Driven Structural Transformation in Carbon Nitride Materials", *Appl. Surface Sci.* 127-129, 569-573, (1998).
Kim, et al., "Charge Density Wave Formation in Nanocrystals", *Solid State Physics*, 55:119-157, H. Enrenreich & F. Spaepen, eds. (Academic Press) 2000.
Lieber, Charles M., "One-Dimensional Nanostructures: Chemistry, Physics & Applications", *Solid State Communications* 107(11):607-616, (1998).

(Continued)

*Primary Examiner*—Kenneth R. Horlick
*Assistant Examiner*—Young J. Kim
(74) *Attorney, Agent, or Firm*—DLA Piper Rudnick Gray Cary US LLP

(57) ABSTRACT

The methods and apparatus 100 disclosed herein are of use for sequencing and/or identifying nucleic acids 230, 310. Nucleic acids 230, 310 containing labeled nucleotides 235, 245, 315 may be synthesized and passed through nanopores 255, 310. Detectors 257, 345 operably coupled to the nanopores 255, 310 may detect the labeled nucleotides 235, 245, 315. By determining the time intervals at which labeled nucleotides 235, 245, 315 are detected, distance maps 140 for each type of labeled nucleotide 235, 245, 315 may be compiled. The distance maps 140 in turn may be used to sequence 150 and/or identify 160 the nucleic acid 230, 310. In different embodiments of the invention, luminescent nucleotides 235, 245 or nanoparticles 315 may be detected using photodetectors 257 or electrical detectors 310. Apparatus 100 and sub-devices 200, 300 of use for nucleic acid 230, 310 sequencing 150 and/or identification 160 are also disclosed herein.

30 Claims, 3 Drawing Sheets

OTHER PUBLICATIONS

Morales, et al., "A Laser Ablation Method for Synthesis of Crystalline Semiconductor Nanowires", *Sci.* 279:208-211, (1998).

Mulvaney, et al., "Glass-Coated, Analyte-Tagged Nanoparticles: A New Tagging System Based on Detection with Surface-Enhanced Raman Scattering", *Am Chem Soc.* 19:4784-4790 (2003).

Noy, et al., "Chemically-Sensitive Imaging in Tapping Mode by Chemical Force Microscopy: Relationship Between Phase Lag and Adhesion", *Langmuir* 14:1508-1511, (1998).

Odom, et al., "Scanning Tunneling Microscopy and Spectroscopy Studies of Single Wall Carbon Nanotubes", *J. Mater. Res.* 13(9):2380-2388, (1998).

Odom, et al., "Magnetic Clusters on Single-Walled Carbon Nanotubes: The Kondo Effect in a One-Dimensional Host", *Sci.* 290:1549-1552, (2000).

Odom, et al., "Structure and Electronic Properties of Carbon Nanotubes", *J. Phys. Chem. B* 104:2794-2809, (2000).

Odom, et al., "Atomic Structure and Electronic Properties of Single-Walled Carbon Nanotubes", *Nature* 391:62-64, (1998).

Rueckes, et al., "Carbon Nanotube-Based Nonvolatile Random Access Memory for Molecular Computing", *Sci.* 289:94-97, (2000).

Vezenov, et al., "Chemical Force Microscopy: Probing and Imaging Interactions Between Functional Groups", *Am. Chem. Soc.* pp. 312-320, (1998).

Wei, et al., "Solution-Based Synthesis of Magnesium Oxide Nanorods", *Mat. Res. Soc. Symp. Proc.* 581:3-7, (2000).

Wei, et al., "Synthesis of Single Crystal Bismuth-Telluride and Lead-Telluride Nanowires for New Thermoelectric Materials", *Mat. Res. Soc. Symp. Proc.* 581:219-223, (2000).

Wooley, et al., "Structural Biology with Carbon Nanotube AFM Probes", *Chem. Biol.* 7(11):R193-R204, (2000).

Wooley, et al., "Direct Haplotyping of Kilobase-Size DNA Using Carbon Nanotube Probes", *Nature Biotechnology* 18:760-763, (2000).

Wong, et al., "Single-Walled Carbon Nanotube Probes for High-Resolution Nanostructure Imaging", *Am. Institute of Physics*, 73(23):3465-3467, (1998).

Wong, et al., "Covalently-Functionalized Single-Walled Carbon Nanotube Probe Tips for Chemical Force Microscopy", *J. Am. Chem. Soc.* 120:8557-8558, (1998).

Wong, et al., "Covalently-Functionalized Nanotubes as Nanometre-sized Probes in Chemistry and Biology", *Nature* 394:52-55, (1998).

Wong, et al., "Carbon Nanotube Tips: High-Resolution Probes for Imaging Biological Systems", *Am. Chem. Soc.* 120:603-604, (1998).

* cited by examiner

METHOD AND APPARATUS FOR NUCLEIC ACID SEQUENCING AND IDENTIFICATION

FIELD OF THE INVENTION

The present invention relates to the fields of molecular biology and analysis of bio-molecules including, but not limited to, nucleic acids. In particular, the invention relates to methods and apparatuses for nucleic acid sequencing and identification.

BACKGROUND OF THE INVENTION

Genetic information is stored in the form of very long molecules of deoxyribonucleic acid (DNA), organized into chromosomes. The human genome contains approximately three billion bases of DNA sequence. This DNA sequence information determines multiple characteristics of each individual. Many common diseases are based at least in part on variations in DNA sequence.

Determination of the entire sequence of the human genome has provided a foundation for identifying the genetic basis of such diseases. However, a great deal of work remains to be done to identify the genetic variations associated with each disease. That would require DNA sequencing of portions of chromosomes in individuals or families exhibiting each such disease, in order to identify specific changes in DNA sequence that promote the disease. Ribonucleic acid (RNA), an intermediary molecule in processing genetic information, may also be sequenced to identify the genetic bases of various diseases.

Existing methods for nucleic acid sequencing, based on detection of fluorescently labeled nucleic acids that have been separated by size, are limited by the length of the nucleic acid that can be sequenced. Typically, only 500 to 1,000 bases of nucleic acid sequence can be determined at one time. This is much shorter than the length of the functional unit of DNA, referred to as a gene, which can be tens or even hundreds of thousands of bases in length. Using current methods, determination of a complete gene sequence requires that many copies of the gene be produced, cut into overlapping fragments and sequenced, after which the overlapping DNA sequences may be assembled into the complete gene. This process is laborious, expensive, inefficient and time-consuming. It also typically requires the use of fluorescent or radioactive labels, which can potentially pose safety and waste disposal problems.

More recently, methods for nucleic acid sequencing have been developed involving hybridization to short oligonucleotides of defined sequenced, attached to specific locations on DNA chips. Such methods may be used to infer short nucleic acid sequences or to detect the presence of a specific nucleic acid in a sample, but are not suited for identifying long nucleic acid sequences.

BRIEF DESCRIPTION OF THE DRAWINGS

The following drawings form part of the specification and are included to further demonstrate certain embodiments of the invention. The embodiments may be better understood by reference to one or more of these drawings in combination with the detailed description presented herein.

DETAILED DESCRIPTION OF THE INVENTION

Definitions

Figure 1:
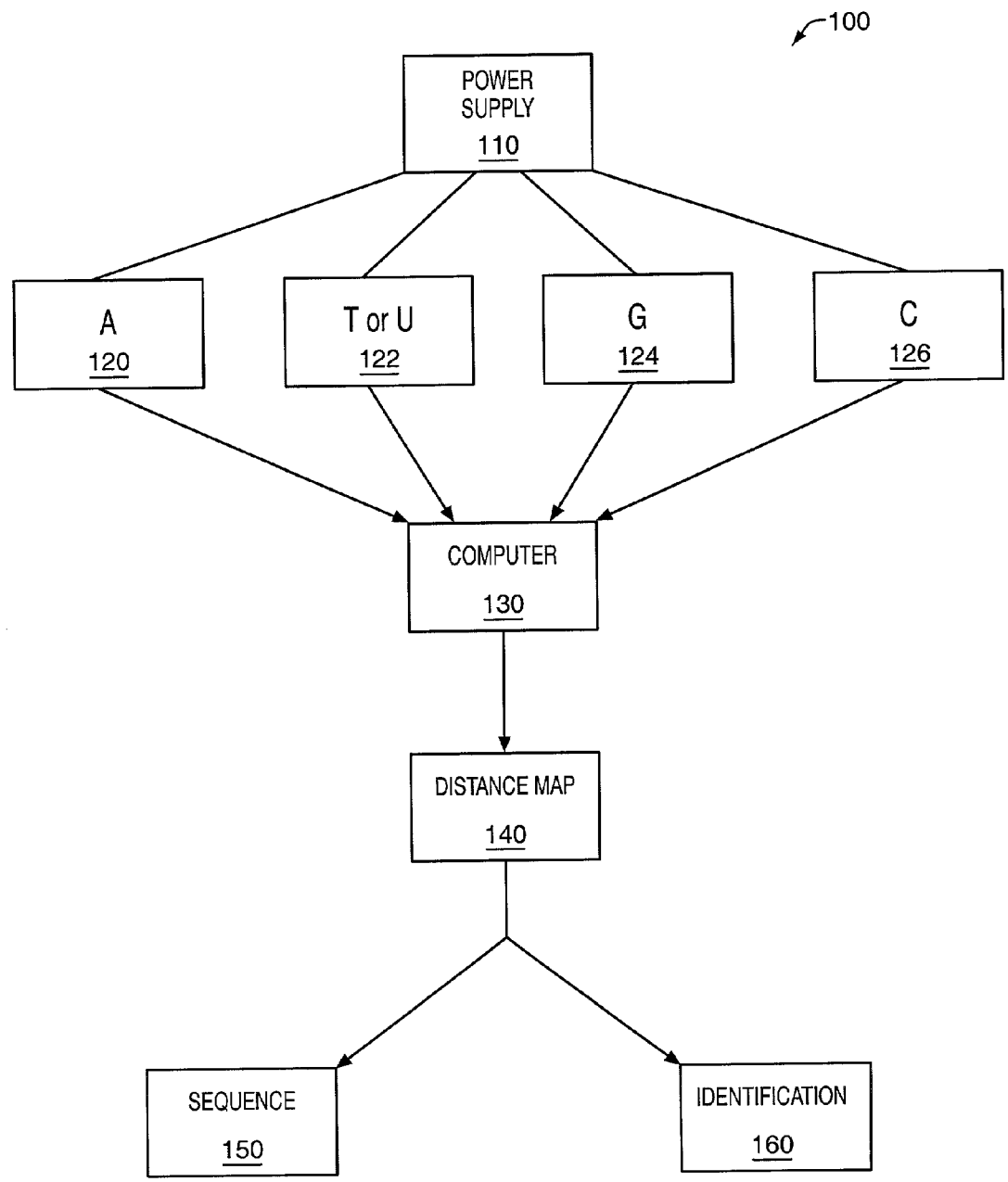
FIG. 1 is a flow chart illustrating an exemplary apparatus 100 (not to scale) and methods for nucleic acid sequencing 150 and/or identification 160 by generation of distance maps 140.

As used herein, "a" or "an" may mean one or more than one of an item.

"Detector" 257, 345 is used herein to mean a device that can detect a signal. The signal to be detected may comprise, but is not limited to, an electrical, conductive, resistive, voltage, current, electromagnetic, optical, luminescent, fluorescent, radioactive, and/or chemical signal.

The terms "nanopore" 255, 330, "nanochannel," and "nanotube" refer respectively to a hole, channel or tube with a diameter or width of between 1 and 999 nanometers (nm). In particular embodiments, the diameter is between 1 and 100 nm. In various embodiments of the invention, "nanopores" 255, 330, "nanotubes" and "nanochannels" may be used interchangeably. The skilled artisan will realize that where the specification refers to a "nanopore," different embodiments of the invention may use a "nanochannel" or "nanotube." The only requirement is that the nanopore 255, 330, nanochannel or nanotube connect one fluid filled compartment to another and allow the passage and detection of labeled nucleic acids 230, 310.

As used herein, "operably coupled" means that there is a functional interaction between two or more units. For example, a detector 257, 345 may be "operably coupled" to a nanopore 255, 330 if the detector 257, 345 is arranged so that it may identify labeled nucleotides 235, 245, 315 passing through the nanopore 255, 330. Similarly, a nanopore 255, 330 may be operably coupled to a chamber 120, 122, 124, 126, 280, 350 if nucleic acids 230, 310 in the chamber can pass through the nanopore 255, 330.

As used herein, "fluid communication" refers to a functional connection between two or more compartments that allows fluids to pass between the compartments. For example, a first compartment is in "fluid communication" with a second compartment if fluid may pass from the first compartment to the second and/or from the second compartment to the first compartment.

"Nucleic acid" 230, 310 encompasses DNA, RNA, single-stranded, double-stranded or triple-stranded and any chemical modifications thereof. Virtually any modification of the nucleic acid 230, 310 is contemplated. As used herein, a single-stranded nucleic acid 230, 310 may be denoted by the prefix "ss", a double-stranded nucleic acid 230, 310 by the prefix "ds", and a triple-stranded nucleic acid 230, 310 by the prefix "ts." A "nucleic acid" 230, 310 may be of almost any length, from 10, 20, 50, 100, 200, 300, 500, 750, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500, 000, 1,000,000, 2,000,000, 5,000,000 or even more bases in length, up to a full-length chromosomal DNA molecule.

A "nucleoside" is a molecule comprising a purine or pyrimidine base, such as adenine—"A" 120, thymine—"T" 122, guanine—"G" 124, cytosine—"C" 126 or uracil—"U" 122, covalently attached to a pentose sugar, such as deoxyribose, ribose or derivatives or analogs of pentose sugars.

A "nucleotide" refers to a nucleoside further comprising at least one phosphate group covalently attached to the pentose sugar. In some embodiments of the invention, the nucleotides are ribonucleoside triphosphates or deoxyribonucleoside triphosphates. It is contemplated that various substitutions or modifications may be made in the structure of the nucleotides, so long as they are still capable of being incorporated into a complementary nucleic acid 230, 310 by a polymerase. For example, in certain embodiments of the invention, the ribose or deoxyribose moiety may be substituted with another pentose sugar or a pentose sugar analog. In other embodiments of the invention, the phosphate groups may be substituted by various groups, such as phosphonates, sulphates or sulfonates. In still other embodiments of the invention, the purine or pyrimidine bases may be substituted by other purines or pyrimidines or analogs thereof, so long as the sequence of nucleotides incorporated into a complementary nucleic acid strand 230, 310 reflects the sequence 150 of the template strand 230, 310.

DESCRIPTION OF ILLUSTRATIVE EMBODIMENTS

The disclosed methods and apparatus 100 are of use for the rapid, automated sequencing 150 and/or identification 160 of nucleic acid molecules 230, 310. Advantages over prior art methods include: high throughput, as fast as $3 \times 10^6$ bases per second ($>3 \times 10^7$ times faster than current methods); ultra-sensitive detection of single labeled nucleic acid molecules 230, 310; nanometer scale resolution of nucleic acid base distances; and lower unit cost of nucleic acid 230, 310 sequencing 150 and/or identification 160.

In some embodiments of the invention, exemplified in FIG. 1, a template nucleic acid 230, 310 is placed into four chambers 120, 122, 124, 126, 280, 350, each chamber 120, 122, 124, 126, 280, 350 to contain a different labeled nucleotide 235, 245, 315—A, G, C and T or U. Labeled complementary nucleic acid strands 230, 310 are synthesized from the template nucleic acids 230, 310 using known synthetic techniques. The labeled nucleic acids 230, 310 from each chamber 120, 122, 124, 126, 280, 350 are passed through one or more nanopores 255, 330, operably coupled to detectors 257, 345 that can detect labeled nucleotides 235, 245, 315. Each chamber 120, 122, 124, 126, 280, 350 is associated with a different set of nanopores 255, 330. The distances between labeled nucleotides 235, 245, 315 are measured to compile a map of distances 140 for each type of labeled nucleotide 235, 245, 315. The distance maps 140 are used to identify 160 or sequence 150 the template nucleic acid 230, 310. In some embodiments of the invention, the nanopore 255, 330 is of a diameter that restricts passage to an individual single- or double-stranded nucleic acid molecule 230, 310. In such embodiments, only one labeled nucleic acid 230, 310 passes through a nanopore 255, 330 at one time. The skilled artisan will realize that although FIG. 2 and FIG. 3 refer to nanopores 255, 330, different embodiments of the invention could utilize nanochannels or nanotubes in place of the nanopores 255, 330.

Figure 2:
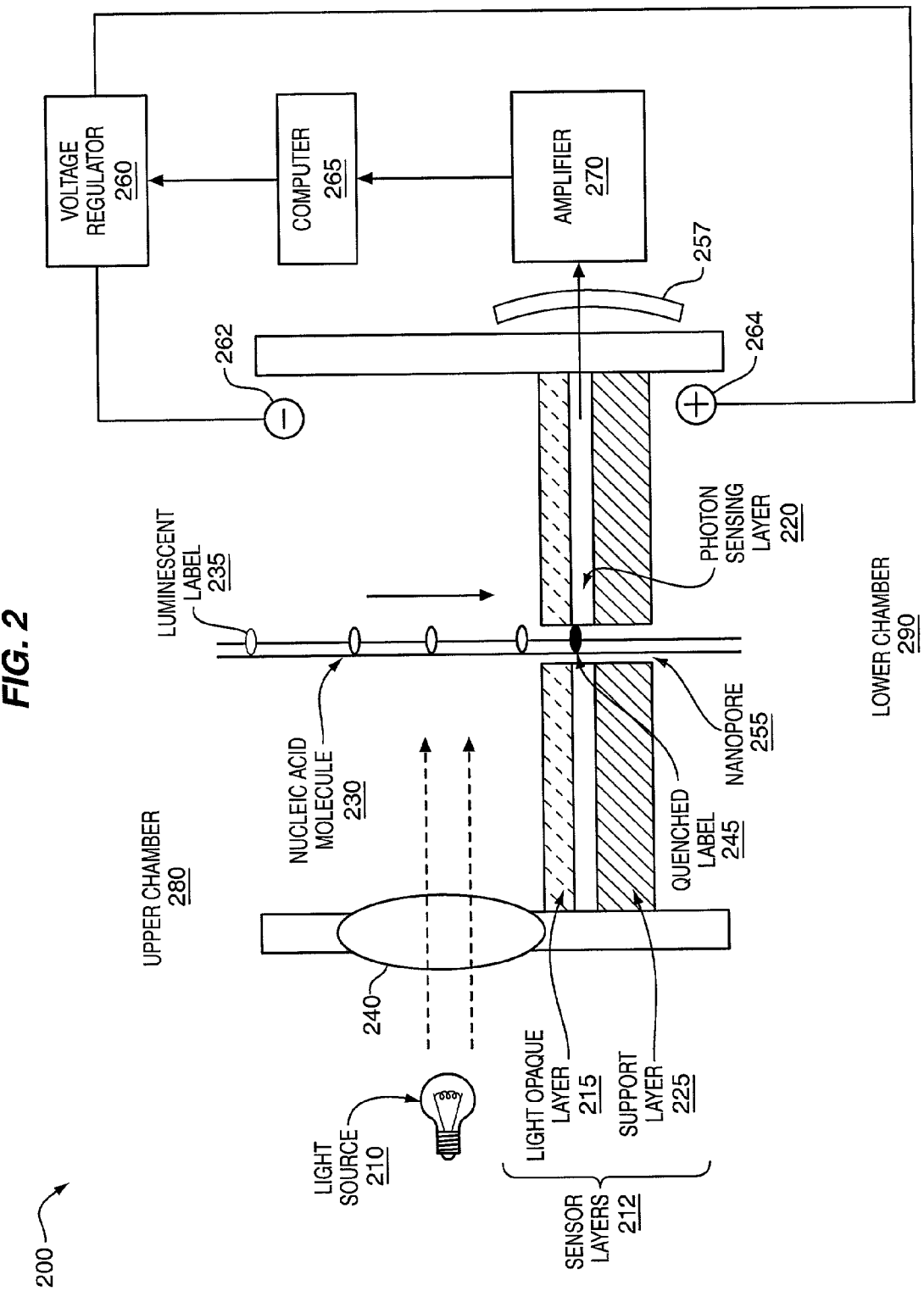
FIG. 2 illustrates a non-limiting example of a sub-device 200 (not to scale) for nucleic acid sequencing 150 and/or identification 160 by photodetection.
Figure 3:
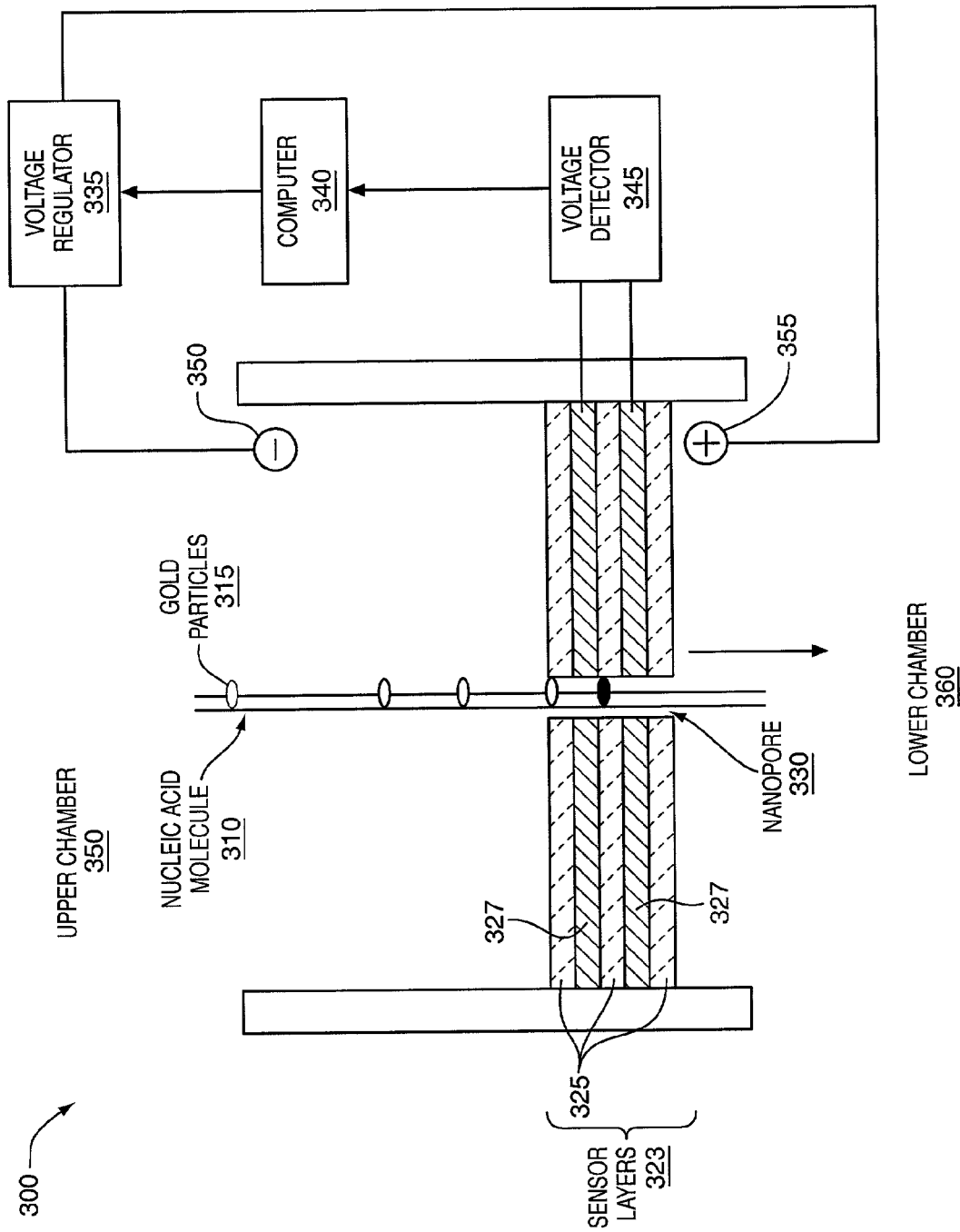
FIG. 3 illustrates another non-limiting example of a sub-device 300 (not to scale) for nucleic acid sequencing 150 and/or identification 160 by electrical detection.

Certain embodiments of the invention concern an apparatus 100 for sequencing 150 and/or identification 160 of nucleic acids 230, 310. In various embodiments of the invention, the apparatus 100 may comprise one or more sub-devices 200, 300, as illustrated in FIG. 2 and FIG. 3. Each sub-device 200, 300 comprises fluid filled upper 280, 350 and lower 290, 360 chambers, separated by sensor layers 212, 323. One or more nanopores 255, 330 extend through the sensor layers 212, 323 and allow passage of nucleic acids 230, 310. The nanopores 255, 330 are operably coupled to one or more detectors 257, 345 that can detect labeled nucleotides 235, 245, 315 as they pass through the nanopores 255, 330. In some embodiments of the invention, electrodes 262, 264, 350, 355 in the upper and lower chambers 280, 350, 290, 360 generate an electrical field that drives labeled nucleic acids 230, 310 from the upper 280, 350 to the lower chamber 290, 360 through the nanopores 255, 330. The electrical gradient may be controlled by a voltage regulator 260, 335, which may be operably coupled to a computer 130, 265, 340.

In alternative embodiments of the invention, detection may occur by either photodetection or electrical detection of labeled nucleotides 235, 245, 315. In embodiments involving photodetection (FIG. 2), the sensor layers 212 may comprise one or more support layers 225, photon-sensing layers 220, and light opaque layers 215. Nucleotides labeled with a luminescent label 235 may be excited by a light source 210, such as a laser. Excitatory light may pass through a transparent window 240 in the upper chamber 280, exciting the luminescent label 235 to a higher energy state. In certain embodiments of the invention, the window 240 may comprise one or more filters and/or lenses to focus the excitatory light. The labeled nucleotide 235, 245 passes through the light opaque layer 215, cutting off the source 210 of excitatory light and shielding the photodetector 257 from the light source 210. As the luminescent label 235 passes the photon sensing layer 220, it emits a photon and becomes quenched 245. In alternative embodiments of the invention involving fluorescence resonance energy transfer FRET, quenching of the excited luminescent label 235 (donor molecule) may occur by interaction with one or more fixed fluorescence acceptor molecules located at the photon sensing layer 220. The emitted photon is transmitted through the photon sensing layer 220 to a photodetector 257, where the signal is detected. The detected signal may be amplified by an amplifier 270 and stored and/or processed by a computer 265. The computer 265 may also record the time at which each labeled nucleotide 235, 245 passes through the nanopore 255, allowing the calculation of distances between adjacent labeled nucleotides 235, 245 and the compilation of a distance map 140 for each sub-device 200.

In other alternative embodiments of the invention (FIG. 3), the sensor layers 325 may comprise at least two insulating layers 325 and at least one conducting layer 327. Typically, insulating layers 325 would be exposed to the medium in the upper 350 and lower 360 buffer chambers, insulating the conducting layers 327 from the external electrical field imposed by the electrodes 350, 355. The conducting layer 327 may be operably coupled to an electrical detector 345, which may detect any type of electrical signal, such as voltage, conductivity, resistance, capacitance, etc. In such embodiments, the nucleotides may be labeled with a label 315 that can be detected by its electrical properties. In one non-limiting example, the label 315 may comprise gold nanoparticles. As a nucleotide labeled with a gold nanoparticle 315 passes through the nanopore 330, it produces changes in the conductivity, resistance and other electrical properties of the nanopore 330 compared to unlabeled portions of the nucleic acid 310. Thus, passage of labeled nucleotides 315 through the nanopore 330 can be detected by the electrical detector 345, just as luminescent labels 235, 245 can be detected by a photodetector 257. Signals detected by the electrical detector 345 may be processed and/or stored by a computer 340. Distance maps 140 between labeled nucleotides 315 may be compiled and the nucleic acid 310 sequenced 150 and/or identified 160.

Nanopores, Nanochannels and Nanotubes

Size Characteristics

In certain embodiments of the invention, the nanopore 255, 330 may be 0.5, 1, 2, 3, 4, 5, 6, 7, 8, 9 or 10 nm in diameter. In other embodiments of the invention, the diameter may range between 1–3, 1–5, 1–10, 1–20, 1–50, 1–100, 5–10, 5–20, 10–20, 20–50, 30–75, 50–75, 50–100, 75–100, 200–300, 300–400, 400–500 or 100–999 nm. A nanopore 255, 330 of approximately 2.6 nm will permit passage of an individual nucleic acid molecule 230, 310. In embodiments of the invention where the nucleotides are labeled 235, 245, 315 with bulky groups, the nanopores 255, 330 may be larger to allow passage of labeled nucleic acids 230, 310. In alternative embodiments of the invention that utilize nanotubes or nanochannels in place of nanopores 255, 330, the same size ranges apply to the diameter or width of the nanotubes or nanochannels.

Fabrication

Fabrication of nanopores 255, 330, nanotubes and/or nanochannels, individually or in arrays, may utilize any technique known in the art for nanoscale manufacturing. The following techniques are exemplary only. In certain embodiments of the invention, nanopores 255, 330, nanochannels and/or nanotubes may be constructed on a solid-state matrix comprising sensor layers 212, 323 by known nanolithography methods, including but not limited to chemical vapor deposition, electrochemical deposition, chemical deposition, electroplating, thermal diffusion and evaporation, physical vapor deposition, sol-gel deposition, focused electron beam, focused ion beam, molecular beam epitaxy, dip-pen nanolithography, reactive-ion beam etching, chemically assisted ion beam etching, microwave assisted plasma etching, electro-oxidation, scanning probe methods, chemical etching, laser ablation, or any other method known in the art (E.g., U.S. Pat. No. 6,146,227).

In various embodiments of the invention, the sensor layers 212, 323 may comprise semiconductor materials including, but not limited to, silicon, silicon oxide, silicon dioxide, germanium, gallinium arsenide, and metal-based compositions such as metals and/or metal oxides. In some embodiments of the invention, sensor layers 212, 323 may be processed by electronic beam, ion beam and/or laser lithography and etching to create a channel, groove, or hole. In other embodiments of the invention, the channel, hole or groove may be coated with an organic or inorganic deposit to reduce the diameter of the channel, hole or groove, or to endow the resultant nanopore 255, 330, nanotube and/or nanochannel with certain physico-chemical characteristics, such as hydrophilicity. Conducting layers 327 comprising metals may be deposited onto a semiconductor surface by means of field evaporation from a scanning tunnel microscopy (STM) or atomic force microscopy (AFM) tip or from a solution or other known methods of metal deposition. Insulating layers 325 may be formed by oxidizing the semiconductor's surface to an insulating composition or by deposition of known insulators.

In certain embodiments of the invention, channels or grooves may be etched into a semiconductor surface by various techniques known in the art including, but not limited to, methodologies using an STM/AFM tip in an oxide etching solution. After channels are formed, two semiconductor surfaces may be opposed to create a plurality of nanopores 255, 330 that penetrate the semiconductor. Such nanopores 255, 330 may be of a size that restricts passage to single nucleic acid molecules 230, 310. In other embodiments of the invention, STM tip methodologies may be used to create nanopores 255, 330, nanodetectors 257, 345, nanosensors, nanowires, nanoleads, nanochannels, and other nanostructures using techniques known in the art. In alternative embodiments of the invention, scanning probes, chemical etching techniques, and/or micromachining may be used to cut micrometer-dimensioned or nanometer-dimensioned channels, grooves or holes in a semiconductor substrate.

In certain embodiments of the invention, nano-molding may be employed, wherein formed nanotubes, such as carbon or metallic nanotubes, are placed or grown on a semiconductor chip substrate. After depositing layers on the substrate, the nanotubes are removed, leaving a nanochannel and/or nanopore 255, 330 imprint in the substrate material. Such nanostructures can be built in clusters with properties of molecular electrodes that may function as detectors 257, 345 on a chip.

In some embodiments of the invention, nanopores 255, 330 and/or nanochannels may be made using a high-throughput electron-beam lithography system, e.g. see world wide web at mdatechonolog.net/techsearch.asp?articleid=510. Electron-beam lithography may be used to write features as small as 5 nm on silicon chips. Sensitive resists, such as polymethyl-methacrylate, coated on silicon surfaces may be patterned without use of a mask. The electron-beam array may combine a field emitter cluster with a microchannel amplifier to increase the stability of the electron beam, allowing operation at low currents. In some embodiments of the invention, the SoftMask3 computer control system may be used to control electron-beam lithography of nanoscale features on a semiconductor chip substrate.

In alternative embodiments of the invention, nanopores 255, 330 and/or nanochannels may be produced using focused atom lasers (e.g., Bloch et al., "Optics with an atom laser beam," *Phys. Rev. Lett.* 87:123–321, 2001). Focused atom lasers may be used for lithography, much like standard lasers or focused electron beams. Such techniques are capable of producing micron scale or even nanoscale structures on a chip. In other alternative embodiments of the invention, dip-pen nanolithography may be used to form nanopores 255, 330 and/or nanochannels (e.g., Ivanisevic et al., "Dip-Pen Nanolithography on Semiconductor Surfaces," *J. Am. Chem. Soc.*, 123: 7887–7889, 2001). Dip-pen nanolithograpy uses AFM techniques to deposit molecules on surfaces, such as silicon chips. Features as small as 15 nm in size may be formed, with spatial resolution of 10 nm. Nanoscale pores 255, 330 and/or channels may be formed by using dip-pen nanolithography in combination with regular photolithography techniques. For example, a micron scale line in a layer of resist may be formed by standard photolithography. Using dip-pen nanolithography, the width of the line and the corresponding diameter of the channel after etching may be narrowed by depositing additional resist compound. After etching of the thinner line, a nanoscale channel may be formed. Alternatively, AFM methods may be used to remove photoresist material to form nanometer scale features.

In other embodiments of the invention, ion-beam lithography may be used to create nanopores 255, 330 and/or nanochannels on a chip (e.g., Siegel, "Ion Beam Lithography," VLSI Electronics, Microstructure Science, Vol. 16, Einspruch and Watts eds., Academic Press, New York, 1987). A finely focused ion beam may be used to write nanoscale features directly on a layer of resist without use of a mask. Alternatively, broad ion beams may be used in combination with masks to form features as small as 100 nm in scale. Chemical etching, for example, with hydrofluoric acid, is used to remove exposed silicon or other chip material that is not protected by resist. The skilled artisan will realize that the techniques disclosed above are not limiting, and that nanopores 255, 330 and/or nanochannels may be formed by any method known in the art.

Carbon Nanotubes

In some embodiments of the invention, the nanopores 255, 330 may comprise, be attached to or be replaced by nanotubes, such as carbon nanotubes. In various embodiments of the invention, the carbon nanotubes may be coated with an organic or inorganic composition, leaving a deposited layer "mold" on the carbon nanotube. When the nanotube is removed and separated from the organic or inorganic deposit, a nanopore 255, 330 may be created in the "mold." Carbon nanotubes may be formed in a semiconductor with other components, such as sensor layers 212, 325, formed around the nanotubes.

In certain embodiments of the invention, carbon nanotubes may be manufactured by chemical vapor deposition (CVD), using ethylene and iron catalysts deposited on silicon (e.g., Cheung et al., PNAS 97:3809–3813, 2000). Single-wall carbon nanotubes may be formed on silicon chips by CVD using AFM $Si_3N_4$ tips (e.g., Cheung, et al., 2000; Wong, et al., Nature 394:52–55, 1998). A flat surface of 1–5 $\mu m^2$ is created on the silicon AFM tips by contact with silicon or CVD diamond surfaces (GE Suprabrasives, Worthington, Ohio) at high load (~1 $\mu N$), at high scan speed (30 Hz), and with a large scan size (40 $\mu m$) for several minutes. Approximate 100 nm diameter, 1 $\mu m$ deep pores in the ends of the AFM tips are made by anodization at 2.1 V for 100 sec. Anodized tips may be etched in 0.03% KOH in water for 50 sec, after which excess silicon is removed with ethanol and nanopores 355, 330 opened at the surface of the tip.

Carbon nanotubes may be attached to AFM tips using known methods. For example, iron catalyst consisting of iron oxide nanoparticles may be synthesized according to Murphy et al. (Austr. J. Soil Res. 13:189–201, 1975). Iron catalyst (0.5 to 4 nm particles) may be electrochemically deposited from a colloidal suspension into the pores using platinum counter electrodes at –0.5 V (Cheung, et al., 2000). Tips may be washed in water to remove excess iron oxide particles. AFM tips may be oxidized by heating in oxygen gas and carbon nanotubes may be grown on the catalyst by controlled heating and cooling in the presence of a carbon source (Murphy et al., 1975; Cheung et al., 2000). The diameter of the resulting nanotubes should correspond to the size of the iron oxide catalyst used (0.5 to 4 nm). Individual, single-walled nanotubes prepared under these conditions are aligned perpendicular to the flattened surface of the AFM tip. Residual iron catalyst may be removed by known methods.

Nanotubes may be cut to a predetermined length using known techniques. In some embodiments of the invention, carbon nanotubes may be attached to pyramids of gold-coated silicon cantilevers using an acrylic adhesive. The carbon nanotubes may be shortened to a defined length by application of a bias voltage between the tip and a niobium surface in an oxygen atmosphere (Wong, et al., Nature 394:52–55, 1998). In other embodiments of the invention, high-energy beams may be used to shorten carbon nanotubes. Such high energy beams may include, but are not limited to, laser beams, ion beams, and electron beams. Alternative methods for truncating carbon nanotubes are known in the art (e.g., U.S. Pat. No. 6,283,812). In other embodiments of the invention, preformed carbon nanotubes may be attached to a chip material such as silicon, glass, ceramic, germanium, polystyrene, and/or gallium arsenide (e.g., U.S. Pat. Nos. 6,038,060 and 6,062,931).

In certain embodiments of the invention, a first set of carbon nanotubes may be used as cold cathode emitters on semiconductor chips, associated with a second set of nanotubes containing nucleic acids 230, 310. The first set of nanotubes may be used to create local electrical fields of at least $10^6$ volts/cm, when an external voltage of between 10 and 50 volts is applied. Such an electric field in the first set of nanotubes can be used to drive nucleic acids 230, 310 through the second set of nanotubes, or to generate an electrical or electromagnetic signal to detect labeled nucleotides 230, 245, 315 (see Chuang, et al., 2000; U.S. Pat. No. 6,062,931). In some embodiments of the invention, a first set of nanotubes that act as detectors 257, 345, electromagnetic conduits or optical devices may be operably coupled to a second set of nanotubes containing labeled nucleic acids 230, 310. In certain embodiments, the nanotubes may be placed in operable contact with each other or with other elements such as detectors 257, 345 by known nanomanipulation techniques. In some embodiments of the invention, each nanotube in the first set is coupled operably to a nanotube in the second set, such that the nanotubes are positioned perpendicular to or otherwise arranged with respect to each other.

In certain embodiments of the invention, electromagnetic radiation from a third set of nanotubes may excite a light-sensitive (e.g., luminescent, fluorescent, phosphorescent) label 235, 245 attached to a nucleic acid 230 passing through a second set of nanotubes, leading to emission of light detected by a photodetector 257 that is operably coupled to a first set of nanotubes.

Ion Channels on Semiconductor Chips

In some embodiments of the invention, nanopores 255, 330 may be single ion channels in lipid bilayer membranes (e.g., Kasianowitz, et al., Proc. Natl. Acad. Sci. USA 93:13770–13773, 1996). Such ion channels may include, but are not limited to, *Staphylococcus aureus* alpha-hemolysin and/or mitochondrial voltage-dependent anion channels. These ion channels may remain open for extended periods of time, allowing continuous current to flow across the lipid bilayer. An electric field applied to single-stranded RNA and DNA molecules 230, 310 can cause these molecules to move through 2.6 nm diameter ion channels in lipid bilayer membranes (Kasianowitz et al., 1996). The single-stranded nucleic acids 230, 310 may pass through the ion channel in linear fashion. Ion channels may be incorporated into chips and operably coupled to detectors 257, 345.

Micro-Electro-Mechanical Systems (MEMS)

Micro-Electro-Mechanical Systems (MEMS) are integrated systems comprising mechanical elements, detectors 257, 345, switches, diodes, transistors, valves, gears, mirrors, actuators, and electronics. All of those components may be manufactured by known microfabrication techniques on a common chip, comprising a silicon-based or equivalent substrate (e.g., Voldman et al., *Ann. Rev. Biomed. Eng.* 1:401–425, 1999). The detector 257, 345 component of MEMS may be used to measure mechanical, thermal, biological, chemical, optical and/or magnetic phenomena. The electronics may process the information from the sensors and control actuator components such pumps, valves, heaters, coolers, filters, etc. thereby controlling the function of the MEMS.

The electronic components of MEMS may be fabricated using integrated circuit (IC) processes (e.g., CMOS, Bipolar, or BICMOS processes). They may be patterned using photolithographic and etching methods known for computer chip manufacture. The micromechanical components may be fabricated using compatible "micromachining" processes that selectively etch away parts of the silicon wafer or add new structural layers to form the mechanical and/or electromechanical components. Basic techniques in MEMS manufacture include depositing thin films of material on a substrate, applying a patterned mask on top of the films by photolithograpic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Sensor layers 212, 325 of 5 nm thickness or less may be formed by such known techniques. Standard lithography techniques may be used to create sensor layer 212, 325 areas of micron or sub-micron dimensions, operably connected to detectors 270, 345 and nanopores 255, 330.

The manufacturing method is not limiting and any methods known in the art may be used, such as atomic layer deposition, pulsed DC magnetron sputtering, vacuum evaporation, laser ablation, injection molding, molecular beam epitaxy, dip-pen nanolithograpy, reactive-ion beam etching, chemically assisted ion beam etching, microwave assisted plasma etching, focused ion beam milling, electron beam or focused ion beam technology or imprinting techniques. Methods for manufacture of nanoelectromechanical systems may be used for certain embodiments of the invention. (See, e.g., Craighead, Science 290:1532–36, 2000.) Various forms of microfabricated chips are commercially available from, e.g., Caliper Technologies Inc. (Mountain View, Calif.) and ACLARA BioSciences Inc. (Mountain View, Calif.).

In various embodiments of the invention, it is contemplated that some or all of the components of the nucleic acid sequencing apparatus 100 exemplified in FIG. 1, FIG. 2 and FIG. 3 may be constructed as part of an integrated MEMS device. In certain embodiments of the invention, nanoelectrodes comprising conducting metals such as gold, platinum, or copper may be operably coupled to nanopores 255, 330, nanochannels and/or nanotubes using STM technologies known in the art (e.g., Kolb et al., Science 275:1097–1099, 1997). Nanoelectrodes, detectors 257, 345 and other components may be connected by nanowires.

In particular embodiments of the invention (FIG. 3), standard photolithography may be used to create an array of multiplaner structures (0.5×0.5 $\mu$m) on a silica substrate, each structure with a silica base support and two layers of gold films 327 separated by an insulator layer 325 comprising silica oxide, with another insulator layer 325 overlaying the top gold film 327. A chip containing the structures may be divided in half and placed on its side. A thin layer of resist may be coated on the sides of the chip, perpendicular to the conducting and insulating layers 325, 327. An AFM/STP tip may be used to etch 5–10 nm lines in the resist layer, overlaying each structure. Chemical etching may be used to create nano-scale grooves in each of the structures. When the halves of the chip are aligned and fused together, the grooves form nanopores 255, 330 and/or nanochannels which extend through the sensor layers 323. Nanowires connecting the conducting layers 327 to electrical detectors 345 may be formed by known methods discussed above. The nanowires may be used to apply a voltage across the conducting layers 327 and changes in current, resistance or other electrical properties may be detected with the passage of a nucleic acid 310 through the nanopore 330. In certain embodiments of the invention, a thin layer of insulating material may be coated onto the sides of the divided chip, forming a barrier that prevents current flow except through the nanopore 330. In embodiments involving photodetection instead of electrical detection, the conducting and insulating layers 325, 327 may be replaced with light opaque and photon sensing layers 210, 220. In certain embodiments, polymeric materials may be coated onto the chip to enhance detectability of signals. Such polymeric materials may include, but are not limited to, polymethylmethacrylate, ultraviolet-curable polyurethanes and epoxies, and other polymers that exhibit optical transparency, low fluorescence at excitation wavelengths, electrical conductivity and/or insulation. Such materials may be formed into appropriate structures, for example by polymer casting and chemical or photochemical curing (Kim et al., Nature 376: 581–584 1995).

Detectors

Electrical Detectors

In certain embodiments of the invention, the detector 345 may detect electrical signals induced in a conducting layer 327 as a function of the passage of a labeled nucleic acid 310 through a nanopore 330. Non-limiting examples of electrical signals include induced current, voltage, impedance, induced electromotive force, signal sign, frequency or noise signature of a predetermined electrical signal generated at one location and received at another location. In some embodiments of the invention, a voltage detector 345 may be operably coupled to one or more conducting layers 327, a power supply and one or more nanopores 330 perpendicular to and penetrating the conducting layers 327. The detector 345 may comprise an ammeter, voltmeter, capacitance meter and/or conductivity meter to measure induced current, voltage, resistance, etc. In certain embodiments, other electrical components such as resistors or capacitors may be included in the electrical circuit associated with the detector 345.

In some embodiments of the invention, the upper and lower chambers 350, 360 may be filled with a low conductivity aqueous buffer. An electrical potential may be applied to the conducting layers 327 flanking a nanopore 330. When buffer alone is present, the resistance between the conducting layers 327 is high. The presence of unlabeled regions of nucleic acids 310 passing through the nanopore 330 would produce a slight increase in conductivity across the nanopore 330, due to the present of conjugated pi electrons and charged groups, such as phosphates. The passage of nucleotides labeled with highly conductive labels 315, such as metal nanoparticles, would result in a large increase in conductivity that produces a detectable signal at the detector 345. In certain embodiments, the nanoparticle labels 315 may be about 1 nm diameter gold nanoparticles 315. The time interval between electrical signals may be measured and used to create a distance map 140 representing the positions of labeled nucleotides 315 on the nucleic acid molecule 310. By compiling such maps for each of the four types of labeled nucleotides in the different sub-chambers 120, 122, 124, 126, it is possible to determine a complete sequence 150 of the nucleic acid 310 and/or to identify 160 the nucleic acid 310.

In particular embodiments of the invention, the upper and lower chambers 350, 360 may be filled with 1 M KCl, 5 mM Hepes pH 7.5. A 2 to 3 nm nanopore 330 may provide fluid communication between the upper and lower chambers 350, 360. Nucleic acids 310 labeled with 1 nm gold nanoparticles 315 may be synthesized and/or placed in the upper chamber 350. A detector 345 and power supply may be operably coupled to conducting layers 327 flanking the nanopore. Current across the nanopore 330 may be converted to voltage and amplified using an Axopatch 200A (Axon Instruments, Foster City, Calif.) or a Dagan 3900A patch clamp amplifier (Dagan Instruments, Minneapolis, Minn.). The signal may be filtered using a Frequency Devices (Haverhill, Mass.) low pass Bessel filter. Data may be digitized using a National Instruments (Austin, Tex.) AT-MIO-16-X 16-bit board and LAB WINDOWS/CVI programs. The chip may be shielded from electric and magnetic noise sources using a mu-metal box (Amuneal, Philadelphia, Pa.) (see Kasianowicz, et al., 1996).

In this non-limiting example, the absence of a nucleic acid 310 in the nanopore 330 results in single channel currents that are free of transient fluctuations when a potential of about −120 mV is applied. After entry of the nucleic acid molecule 310 into the nanopore 330, current blockage patterns are measured. Labeled nucleotides 315 attached to 1.0 nm gold particles exhibit greater current fluctuations that are detectable over unlabeled nucleic acid 310 regions. Nucleic acid sequences may be obtained by comparing distance maps 140 for each sub-chamber 120, 122, 124, 126.

Spectrophotometric Detection

In alternative embodiments of the invention, labeled nucleotides 235 may be detected using a light source 210 and photodetector 257, such as a diode-laser illuminator 210 and fiber-optic or phototransistor detector 257. (E.g., Sepaniak et al., J. Microcol. Separations 1:155–157, 1981; Foret et al., Electrophoresis 7:430–432, 1986; Horokawa et al., J. Chromatog. 463:39–49 1989; U.S. Pat. No. 5,302,272.) Other exemplary light sources 210 include vertical cavity surface-emitting lasers, edge-emitting lasers, surface emitting lasers and quantum cavity lasers, for example a Continuum Corporation Nd-YAG pumped Ti:Sapphire tunable solid-state laser and a Lambda Physik excimer pumped dye laser. Other exemplary photodetectors 257 include photodiodes, avalanche photodiodes, photomultiplier tubes, multianode photomultiplier tubes, phototransistors, vacuum photodiodes, silicon photodiodes, and charge-coupled devices (CCDs).

In some embodiments of the invention, the photodetector 257, light source 210, and nanopore 255 may be fabricated into a semiconductor chip using known N-well Complementary Metal Oxide Semiconductor (CMOS) processes (Orbit Semiconductor, Sunnyvale, Calif.). In alternative embodiments of the invention, the detector 257, light source 210 and nanopore 255 may be fabricated in a silicon-on-insulator CMOS process (e.g., U.S. Pat. No. 6,117,643). In other embodiments of the invention, an array of diode-laser illuminators 210 and CCD detectors 257 may be placed on a semiconductor chip (U.S. Pat. Nos. 4,874,492 and 5,061,067; Eggers et al., BioTechniques 17: 516–524, 1994).

In certain embodiments of the invention, a highly sensitive cooled CCD detector 257 may be used. The cooled CCD detector 257 has a probability of single-photon detection of up to 80%, a high spatial resolution pixel size (5 microns), and sensitivity in the visible through near infrared spectra. (Sheppard, Confocal Microscopy: Basic Principles and System Performance in: Multidimensional Microscopy, P. C. Cheng et al. eds., Springer-Verlag, New York, N.Y. pp. 1–51, 1994.) In another embodiment of the invention, a coiled image-intensified coupling device (ICCD) may be used as a photodetector 257 that approaches single-photon counting levels (U.S. Pat. No. 6,147,198). A nanochannel plate operates as photomultiplier tube wherein a small number of photons triggers an avalanche of electrons that impinge on a phosphor screen, producing an illuminated image. This phosphor image is sensed by a CCD chip region attached to an amplifier 270 through a fiber optic coupler. In some embodiments of the invention, a CCD detector 257 on the chip may be sensitive to ultraviolet, visible, and/or infrared spectra light (U.S. Pat. No. 5,846,708).

In some embodiments of the invention, a nanopore 255 containing the labeled nucleic acid 230 may be operably coupled to a light source 210 and a detector 257 on a semiconductor chip. In certain embodiments of the invention, the detector 257 may be positioned perpendicular to the light source 210 to minimize background light. The photons generated by excitation of the luminescent label 235 on the nucleic acid 230 may be collected by a fiber optic. The collected photons are transferred to a CCD detector 257 on the chip and the light detected and quantified. The times at which labeled nucleotides 235 are detected may be recorded and nucleotide distance maps 140 may be constructed. Methods of placement of optical fibers on a semiconductor chip in operable contact with a CCD detector 257 are known (U.S. Pat. No. 6,274,320).

In some embodiments of the invention, an avalanche photodiode (APD) 257 may be used to detect low light levels. The APD process uses photodiode arrays 257 for electron multiplication effects (U.S. Pat. No. 6,197,503). In other embodiments of the invention, light sources 210, such as light-emitting diodes LEDs and/or semiconductor lasers may be incorporated into semiconductor chips (U.S. Pat. No. 6,197,503). Diffractive optical elements that shape a laser or diode light beam may also be integrated into a chip.

In certain embodiments of the invention, a light source 210 produces electromagnetic radiation that excites a photosensitive label 235, such as fluorescein, attached to the nucleic acid 230. In some embodiments of the invention, an air-cooled argon laser 210 at 488 nm excites fluorescein-labeled 235 nucleic acid molecules 230. Emitted light may be collected by a collection optics system comprising a fiber optic, a lens, an imaging spectrometer, and a 0° C. thermoelectrically-cooled CCD camera 257. Alternative examples of fluorescence detectors 257 are known in the art (e.g., U.S. Pat. No. 5,143,8545).

Raman Spectroscopy

In some embodiments of the invention, labeled nucleotides 235, 245, 315 may be detected by Raman spectroscopy. Raman labels of use in spectrophotometric detection of labeled nucleic acids 230, 310 are well known in the art. (See, e.g., U.S. Pat. Nos. 5,306,403; 6,002,471; 6,174,677.) Labeled nucleotides 235, 245, 315 may be excited with a laser, photodiode, or other light source 210 and the excited nucleotide 235, 245, 315 detected by a variety of Raman techniques, including but not limited to surface enhanced Raman spectroscopy (SERS), surface enhanced resonance Raman spectroscopy (SERRS) normal Raman scattering, resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy. In SERS and SERRS, the sensitivity of the Raman detection is enhanced by a factor of $10^6$ or more for molecules adsorbed on roughened metal surfaces, such as silver, gold, platinum, copper or aluminum surfaces. For such embodiments, portions of the nanopores 255, 330 and/or sensor layers 212, 323 may be coated with a Raman sensitive metal, such as silver or gold to provide an enhanced Raman signal. Alternatively, an enhanced Raman signal may be produced by nucleotides labeled with gold or silver nanoparticles 315.

FRET Detection

In certain alternative embodiments of the invention, a nucleic acid 230 may be identified or sequenced using fluorescence resonance energy transfer (FRET). FRET is a spectroscopic phenomenon used to detect proximity between fluorescent donor and acceptor molecules. The donor and acceptor pairs are chosen such that fluorescent emission from the donor overlaps the excitation spectrum of the acceptor. When the two molecules are associated at a distance of less than 100 Angstroms, the excited-state energy of the donor is transferred non-radiatively to the acceptor and the donor emission is quenched. If the acceptor molecule is a fluorophore then its emission is enhanced. Compositions and methods for use of FRET with oligonucleotides are known (e.g., U.S. Pat. No. 5,866,366).

In certain embodiments of the invention, the donor fluorophore molecules may be attached to a nucleotide 235, 255, and the acceptor fluorophore molecules may be connected to a nanopore 255 or sensor layers 212. Following excitation by a light source 210, the donor fluorophore molecules will transfer their energy to the acceptor molecules, resulting in an enhanced fluorescent signal from the acceptor molecules that may be detected by the detector 257.

Nucleotide Labels

In various embodiments of the invention, labeled nucleotides 235, 245, 315 may be prepared by any methods known in the art. In certain embodiments, a labeled nucleotide 235, 245, 315 may be incorporated into a nucleic acid strand 230, 310 during synthesis. In other embodiments of the invention, labels 235, 245, 315 may be attached by covalent, noncovalent, ionic, van der Waals, hydrogen bonding or other forces following nucleic acid 230, 310 synthesis.

In various embodiments of the invention, detectable labels 235, 245, 315 may include, but are not limited to, any composition detectable by electrical, optical, spectrophotometric, photochemical, biochemical, immunochemical, or chemical techniques. Labels 235, 245, 315 may include, but are not limited to, conducting, luminescent, fluorescent, chemiluminescent, bioluminescent and phosphorescent labels, nanoparticles, metal nanoparticles, gold nanoparticles, silver nanoparticles, chromogens, antibodies, antibody fragments, genetically engineered antibodies, enzymes, substrates, cofactors, inhibitors, binding proteins, magnetic particles and spin labels. (U.S. Pat. Nos. 3,817,837; 3,850,752; 3,939,350; 3,996,345; 4,277,437; 4,275,149; and 4,366,241.) Fluorescent molecules suitable for use as labels 235, 245 include fluorescein, dansyl chloride, rhodamineisothiocyanate, and Texas Red. Luminescent labels 235, 245 include, but are not limited to, rare earth metal cryptates, europium trisbipyridine diamine, a europium cryptat or chelate, Tb tribipyridine, diamine, dicyanins, La Jolla blue dye, allopycocyanin, allococyanin B, phycocyanin C, phycocyanin R, thiamine, phycoerythrocyanin, phycoerythrin R, an up-converting or down-converting phosphor, luciferin, or acridinium esters. A variety of other known fluorescent or luminescent labels 235, 245 may be utilized. (See, e.g., U.S. Pat. No. 5,800,992; U.S. Pat. No. 6,319,668.)

In certain embodiments of the invention, nanoparticles labeled nucleotides 315 may be used. In some embodiments of the invention, the nanoparticles 315 are silver or gold nanoparticles 315, although any nanoparticles 315 capable of providing a detectable signal may be used. In various embodiments of the invention, nanoparticles 315 of between 1 nm and 3 nm in diameter may be used, although nanoparticles 315 of different dimensions and mass are contemplated. Methods of preparing nanoparticles 315 are known. (See e.g., U.S. Pat. Nos. 6,054,495; 6,127,120; 6,149,868; Lee and Meisel, *J. Phys. Chem.* 86:3391–3395, 1982.) Nanoparticles 315 may also be obtained from commercial sources (e.g., Nanoprobes Inc., Yaphank, N.Y.; Polysciences, Inc., Warrington, Pa.). Modified nanoparticles 315 are available commercially, such as Nanogold® nanoparticles 315 from Nanoprobes, Inc. (Yaphank, N.Y.). Nanogold® nanoparticles 315 may be obtained with either single or multiple maleimide, amine or other groups attached per nanoparticle 315. The Nanogold® nanoparticles 315 also are available in either positively or negatively charged form. Such modified nanoparticles 315 may be attached covalently to nucleotides either before or after the nucleotides are incorporated into nucleic acids 330. In certain embodiments of the invention, nanoparticles 315 or other labels may be attached to nucleotides via any known linker compound to reduce steric hindrance and facilitate nucleic acid polymerization.

In certain embodiments of the invention, labeled nucleotides 235, 245, 315 may be incorporated into complementary nucleic acid strands 230, 310 made from a nucleic acid template 230, 310. In other embodiments of the invention, labels 235, 245, 315 may be attached to a particular type of nucleotide after synthesis of the nucleic acid 230, 310. In other embodiments of the invention, the label 235, 245, 315 may be attached by antibody-antigen interactions. In certain embodiments of the invention, a label 235, 245, 315 may be attached to one end of a nucleic acid molecule 230, 310, such as the 5' or the 3' end. In other embodiments of the invention, a fluorescein or biotin label 235, 245 may be attached to the 5' end of the nucleic acid 230, 310 (U.S. Pat. No. 6,344,316).

Nucleic Acids

Template nucleic acid molecules 230, 310 may be prepared by any technique known in the art. In certain embodiments of the invention, the template molecules 230, 310 may be naturally occurring DNA or RNA molecules, for example, chromosomal DNA or messenger RNA mRNA. Virtually any naturally occurring nucleic acid molecules 230, 310 may be prepared and sequenced by the disclosed methods including, without limit, chromosomal, mitochondrial or chloroplast DNA or ribosomal, transfer, heterogeneous nuclear or messenger RNA. Methods for preparing and isolating various forms of cellular nucleic acids 230, 310 are known. (See, e.g., *Guide to Molecular Cloning Techniques*, eds. Berger and Kimmel, Academic Press, New York, N.Y., 1987; *Molecular Cloning: A Laboratory Manual,* 2nd Ed., eds. Sambrook, Fritsch and Maniatis, Cold Spring Harbor Press, Cold Spring Harbor, N.Y., 1989.) The methods disclosed in the cited references are exemplary only and any variation known in the art may be used.

In cases where single stranded DNA (ssDNA) 230, 310 is to be sequenced, an ssDNA 230, 310 may be prepared from double stranded DNA (dsDNA) by any known method. Such methods may involve heating dsDNA and allowing the strands to separate, or may alternatively involve preparation of ssDNA 230, 310 from dsDNA by known amplification or replication methods, such as cloning into M13. Any such known method may be used to prepare ssDNA or ssRNA 230, 310.

Although the discussion above concerns preparation of naturally occurring nucleic acids 230, 310, virtually any type of nucleic acid 230, 310 could be sequenced by the disclosed methods. For example, nucleic acids 230, 310 prepared by various amplification techniques, such as polymerase chain reaction (PCR™) amplification, could be sequenced. (See U.S. Pat. Nos. 4,683,195, 4,683,202 and 4,800,159.) Nucleic acids 230, 310 to be sequenced may alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts 230, 310 may be isolated from vector DNA, for example, by excision with appropriate restriction endonucleases, followed by agarose gel electrophoresis. Methods for isolation of insert nucleic acids 230, 310 are well known.

Nucleic acids 230, 310 to be sequenced may be isolated from a wide variety of organisms including, but not limited to, viruses, bacteria, pathogenic organisms, eukaryotes, plants, animals, mammals, dogs, cats, sheep, cattle, swine, goats and humans. Also contemplated for use are amplified nucleic acids 230, 310 or amplified portions of nucleic acids 230, 310.

Nucleic Acid Amplification

A number of template dependent processes are available to amplify template nucleic acid 230, 310 present in a given sample. One of the best-known amplification methods is the polymerase chain reaction PCR. Another method for nucleic acid 230, 310 amplification is the ligase chain reaction "LCR". In yet another method of nucleic acid 230, 310 amplification, Qbeta Replicase may be used. Strand Displacement Amplification SDA is another method of carrying out isothermal amplification of nucleic acid 230, 310 that involves multiple rounds of strand displacement and synthesis, i.e., nick translation. Other nucleic acid 230, 310 amplification procedures include transcription-based amplification systems TAS, including nucleic acid 230, 310 sequence based amplification (NASBA).

Nucleic Acid Synthesis

Certain embodiments of the invention involve binding of a synthetic reagent, such as a DNA polymerase, to a primer molecule and the addition of labeled nucleotides 235, 245, 315 to the 3' end of the primer. Non-limiting examples of polymerases of potential use include DNA polymerases, RNA polymerases, reverse transcriptases, and RNA-dependent RNA polymerases. The differences between these polymerases in terms of their "proofreading" activity and requirement or lack of requirement for primers and promoter sequences are known in the art. Where RNA polymerases are used as the polymerase, the template molecule 230, 310 to be sequenced may be double-stranded DNA. Methods of using polymerases to synthesize nucleic acids 230, 310 from labeled nucleotides 235, 245, 315 are known. (See, e.g., U.S. Pat. Nos. 4,962,037; 5,405,747; 6,136,543; 6,210,896.)

Primers

Generally, primers are between ten and twenty bases in length, although longer primers may be employed. In certain embodiments of the invention, primers are designed to be exactly complementary in sequence to a known portion of a template nucleic acid 230, 310 molecule. Known primer sequences may be used, for example, where primers are selected for identifying sequence variants adjacent to known constant chromosomal sequences, where an unknown nucleic acid 230, 310 sequence is inserted into a vector of known sequence, or where a native nucleic acid 230, 310 has been sequenced partially. Methods for synthesis of primer of any sequence are known and automated oligonucleotide synthesizers are commercially available See, e.g., Applied Biosystems, Foster City, Calif.; Millipore Corp., Bedford, Mass.

Other embodiments of the invention involve sequencing 150 a nucleic acid 230, 310 in the absence of a known primer-binding site. In such cases, it may be possible to use random primers, such as random hexamers or random oligomers of 7, 8, 9, 10, 11, 12, 13, 14, 15 bases or greater length, to initiate polymerization.

Computer

In certain embodiments of the invention, the sequencing apparatus 100 may comprise a computer 130, 265, 340. The embodiments of the invention are not limiting for the type of computer 130, 265, 340 used. An exemplary computer 130, 265, 340 may comprise a bus for communicating information and a processor for processing information. In one non-limiting example, the processor is selected from a group consisting of a Pentium®, a Celeron®, an Itanium®, an X-scale or a Pentium Xeon® processor (Intel Corp., Santa Clara, Calif.).

The computer 130, 265, 340 may comprise further a random access memory RAM or other dynamic storage device, a read only memory ROM and/or other static storage and a data storage device, such as a magnetic disk or optical disc and its corresponding drive. The computer 130, 265, 340 also may comprise other peripheral devices known in the art, such a display device e.g., cathode ray tube or Liquid Crystal Display, an alphanumeric input device e.g., keyboard, a cursor control device e.g., mouse, trackball, or cursor direction keys and a communication device e.g., modem, network interface card, or interface device used for coupling to Ethernet, token ring, or other types of networks.

In particular embodiments of the invention, the detector 257, 345 may be operably coupled to the computer 130, 265, 340. Data from the detector 257, 345 may be analyzed by the processor and the data stored in the main memory. The processor may compile the data from the detector 257, 345 corresponding to time at which labeled nucleotides 235, 245, 315 pass through a nanopore 255, 330. Data from a plurality of nanopores 255, 330 may be utilized to obtain the complete nucleic acid sequence 150. It is appreciated that a differently equipped computer 130, 265, 340 than the example described above may be used for certain implementations. Therefore, the configuration of the system may vary in different embodiments of the invention.

In certain embodiments of the invention, the computer 130, 265, 340 may control the speed of passage of the nucleic acid molecule 230, 310 through the nanopore 255, 330 by controlling the voltage regulator 260, 335. In certain embodiments of the invention, custom-designed software packages may be used to analyze the data obtained from the detector 257, 345. In alternative embodiments of the invention, data analysis may be performed, using a computer 130, 265, 340 and publicly available software packages. Non-limiting examples of available software for DNA sequence analysis include the PRISM3 DNA Sequencing Analysis Software (Applied Biosystems, Foster City, Calif.), the Sequencher3 package (Gene Codes, Ann Arbor, Mich.), and a variety of software packages available through the National Biotechnology Information Facility.

All of the METHODS and APPARATUS disclosed and claimed herein can be made and executed without undue experimentation in light of the present disclosure. It will be apparent to those of skill in the art that variations may be applied to the METHODS and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A method comprising:
   a) placing a template nucleic acid into four chambers, each chamber being associated with different nanopores and each chamber comprising a different labeled nucleotide;
   b) synthesizing a labeled nucleic acid from the template nucleic acid;
   c) contacting the labeled nucleic acid in each chamber with its associated nanopore, wherein the labeled nucleic acid passes through the associated nanopore;
   d) detecting a labeled nucleotide;
   e) compiling a nucleotide distance map for each type of labeled nucleotide; and
   f) determining the sequence of the nucleic acid from the nucleotide distance maps.

2. The method of claim 1, wherein each nanopore is operably coupled to a detector.

3. The method of claim 1, wherein only one labeled nucleic acid passes through a nanopore at a time.

4. The method of claim 1, wherein a first chamber contains labeled deoxyadenosine-5'-triphosphate, a second chamber contains labeled deoxyguanosine-5'-triphosphate, a third chamber contains labeled deoxycytidine-5'-triphosphate and a fourth chamber contains labeled deoxythymidine-5'-triphosphate or labeled deoxyuridine-5'-triphosphate.

5. The method of claim 1, wherein the labeled nucleotide comprises between about 1% and 50% of the total amount of the nucleotide in said each chamber.

6. The method of claim 5, wherein the labeled nucleotide comprises between about 10% and 20% of the total amount of the nucleotide in said each chamber.

7. The method of claim 1, wherein the length of time between passage of a first-labeled nucleotide and a second labeled nucleotide through a nanopore corresponds to the distance along the labeled nucleic acid between the first and second labeled nucleotides.

8. The method of claim 1, wherein the labels of said labeled nucleotides are selected from the group consisting of luminescent labels, fluorescent labels, phosphorescent labels, chemiluminescent labels, conductive labels, nuclear magnetic resonance labels, mass spectroscopy labels, electron spin resonance labels, electron paramagnetic resonance labels and Raman labels.

9. The method of claim 1, wherein at least one end of the labeled nucleic acid is attached to an identifiable label.

10. The method of claim 1, wherein said labeled nucleic acid comprises luminescent labels and said labeled nucleotides are detected with a photodetector.

11. The method of claim 1, wherein said labeled nucleic acid comprises nanoparticles and said labeled nucleotides are detected with an electrical detector.

12. The method of claim 1, further comprising analyzing a multiplicity of labeled nucleic acids from each chamber.

13. A method comprising:
    a) placing a template nucleic acid into four sub-devices, each sub-device comprising an upper chamber and a lower chamber separated by a sensor layer having one or more nanopores, the upper and lower chambers of each sub-device in fluid communication through the nanopores, and each upper chamber containing a different labeled nucleotide;
    b) synthesizing a labeled nucleic acid from the template nucleic acid in each upper chamber;
    c) passing the labeled nucleic acid in each upper chamber through its associated nanopore;
    d) detecting labeled nucleotides passing through the associated nanopore with a detector, the detector being operably coupled to the associated nanopore; and
    e) compiling a nucleotide distance map for each type of labeled nucleotide.

14. The method of claim 13, further comprising:
    f) determining the sequence of the template nucleic acid from the nucleotide distance maps.

15. The method of claim 13, further comprising:
    f) identifying the template nucleic acid from the nucleotide distance maps.

16. The method of claim 13, wherein only one labeled nucleic acid passes through a nanopore at a time.

17. The method of claim 13, wherein a first upper chamber contains labeled deoxyadenosine-5'-triphosphate, a second upper chamber contains labeled deoxyguanosine-5'-triphosphate, a third upper chamber contains labeled deoxycytidine-5'-triphosphate and a fourth upper chamber contains labeled deoxythymidine-5'-triphosphate or labeled deoxyuridine-5'-triphosphate.

18. The method of claim 13, wherein the labeled nucleotide comprises between about 1% and 50% of the total amount of the nucleotide in said each chamber.

19. The method of claim 13, wherein the length of time between passage of a first-labeled nucleotide and a second labeled nucleotide through a nanopore corresponds to the distance along the labeled nucleic acid between the first and second labeled nucleotides.

20. The method of claim 13, wherein the labels of said labeled nucleotides are selected from the group consisting of luminescent labels, fluorescent labels, phosphorescent labels, chemiluminescent labels, conductive labels, nuclear magnetic resonance labels, mass spectroscopy labels, electron spin resonance labels, electron paramagnetic resonance labels and Raman labels.

21. The method of claim 13, wherein at least one end of the labeled nucleic acid is attached to an identifiable label.

22. The method of claim 13, wherein the labeled nucleic acid comprises luminescent labels and the detector is a photodetector.

23. The method of claim 13, wherein the labeled nucleic acid comprises nanoparticles and the detector is an electrical detector.

24. The method of claim 13, wherein the detector is capable of separately detecting signals from all sub-devices.

25. The method of claim 13, wherein the detector is operably coupled to a computer.

26. The method of claim 13, wherein the sensor layers comprise one or more support layers, photon-sensing layers, and light opaque layers.

27. The method of claim 26, wherein the detector is a photodetector operably coupled to the photon-sensing layer.

28. The method of claim 13, wherein the sensor layers comprise at least two insulating layers and at least one conducting layer.

29. The method of claim 28, wherein the detector is an electrical detector operably coupled to the conducting layer.

30. The method of claim 13, wherein one or more of the sub-devices includes electrodes in the upper and lower chambers operably coupled to a voltage regulator configured to generate an electrical field that drives labeled nucleic acids from the upper to the lower chamber through the nanopores.

* * * * *